United States Patent [19]
Ruiz

[11] Patent Number: 6,120,534
[45] Date of Patent: Sep. 19, 2000

[54] ENDOLUMINAL PROSTHESIS HAVING ADJUSTABLE CONSTRICTION

[76] Inventor: Carlos E. Ruiz, 1747 N. Country La., Pasadena, Calif. 91107

[21] Appl. No.: 08/959,586

[22] Filed: Oct. 29, 1997

[51] Int. Cl.$^7$ ....................................................... A61F 2/06
[52] U.S. Cl. ........................ 623/1.19; 623/1.3; 623/1.15; 606/194
[58] Field of Search ................................ 623/1, 12, 1.18, 623/1.15, 1.19, 1.3, 1.31; 606/108, 192, 194, 195

[56] References Cited

U.S. PATENT DOCUMENTS

| | | | |
|---|---|---|---|
| 3,730,186 | 5/1973 | Edmunds et al. | 128/325 |
| 4,733,665 | 3/1988 | Palmaz | 128/343 |
| 5,197,978 | 3/1993 | Hess | 623/1 |
| 5,219,355 | 6/1993 | Parodi et al. | 606/191 |
| 5,330,500 | 7/1994 | Song | 606/198 |
| 5,421,955 | 6/1995 | Lau et al. | 216/48 |
| 5,476,506 | 12/1995 | Lunn | 623/1 |
| 5,569,295 | 10/1996 | Lam | 623/1 |
| 5,571,173 | 11/1996 | Parodi | 623/1 |
| 5,575,818 | 11/1996 | Pinchuk | 606/195 |
| 5,609,605 | 3/1997 | Marshall et al. | 606/108 |
| 5,609,627 | 3/1997 | Goicoechea et al. | 606/108 |
| 5,618,301 | 4/1997 | Hauenstein et al. | 623/1 |
| 5,667,486 | 9/1997 | Mikulich et al. | 606/195 |
| 5,716,393 | 2/1998 | Lindenberg et al. | 623/1 |
| 5,741,333 | 4/1998 | Frid | 623/1 |
| 5,755,769 | 5/1998 | Richard et al. | 623/11 |
| 5,755,779 | 5/1998 | Horiguchi | 623/1 |
| 5,876,448 | 3/1999 | Thompson et al. | 623/12 |

FOREIGN PATENT DOCUMENTS

| | | | |
|---|---|---|---|
| 0712614A1 | 5/1996 | European Pat. Off. | A61F 2/06 |
| 0732088A2 | 9/1996 | European Pat. Off. | A61F 2/06 |

*Primary Examiner*—Bruce Snow
*Attorney, Agent, or Firm*—Fish & Neave; Nicola A. Pisano

[57] ABSTRACT

Apparatus and methods for regulating the flow of fluids through a body vessel or organ are provided by a stent comprising a deformable mesh covered with a biocompatible material, the mesh having a conical portion and a constricted region. The stent may be percutaneously and transluminally delivered and deployed in a vessel. The constricted region may then be selectively enlarged employing a conventional dilatation device to adjust the flow impedance created by the constricted region. In an alternative embodiment, the constricted region is preferably formed from a shape-memory material, so that the maximum degree of constriction may be recovered by heating the shape-memory material. Methods of implanting the stent and adjusting and optimizing the degree of flow impedance are also provided.

12 Claims, 5 Drawing Sheets

ENDOLUMINAL PROSTHESIS HAVING ADJUSTABLE CONSTRICTION

FIELD OF THE INVENTION

The present invention relates to apparatus and methods for providing an adjustable constriction within a vessel to control flow therethrough. More particularly, the present invention provides an endoluminal prosthesis, and methods of interventional use, for treating pediatric congenital defects heretofore addressed solely by surgical techniques.

BACKGROUND OF THE INVENTION

Despite surgical advances in the early repair of congenital cardiac malformations that cause overloading of pulmonary circulation, the palliative procedure referred to as "Pulmonary Artery Banding" is still performed on several thousand children each year. The procedure is often performed where the cardiac malformations are so complex that staged surgeries are required. The procedure is also performed in cases where, because of the age of the infant, final repair of the anomaly would pose too high a risk of mortality.

Pulmonary Artery Banding is a palliative procedure designed to reduce blood flow through the pulmonary artery, so as to reduce distal pulmonary artery pressure. The procedure is effective in alleviating congestive cardiac failure and protects the pulmonary vasculature from experiencing irreversible increases in hemodynamic resistance. Pulmonary Artery Banding is typically performed through a thoracotomy, and involves placing a band formed from a cotton umbilical tape, woven Dacron® tape, or other material, around the main pulmonary artery. The band is then tightened to constrict the pulmonary artery to a desired diameter.

While Pulmonary Artery Banding presents a relatively low risk of mortality, about 3–5%, it nevertheless has a number of disadvantages and drawbacks. Primary among these drawbacks is the inability of the surgeon performing the procedure to assess, from the hemodynamic standpoint, the optimal final diameter to which the pulmonary artery should be adjusted. Often, the surgeon must rely upon his or her experience in adjusting the band to achieve acceptable forward flow (i.e., to sustain a forward cardiac output), while decreasing the blood flow sufficiently to protect the pulmonary vasculature.

Moreover, there is a risk that the band will erode through the pulmonary artery, thereby causing vessel thrombosis or hemorrhage. It is also not uncommon for the band to migrate towards one of the main pulmonary branches (usually the left), resulting in stenosis of the origin of the other main pulmonary branch (usually the right). In addition, the band must be removed in a subsequent operation, for example, when the malformation is corrected.

Edmunds et al. U.S. Pat. No. 3,730,186 describes an implantable pulmonary artery band including a toroidal balloon occluder that is disposed around the native pulmonary artery. The balloon occluder is inflated via a subcutaneously implanted injection button using a conventional hypodermic needle. A drawback of the Edmunds et al. device is the relative complexity of the device and the need to eventually remove the device once the congenital malformation is corrected.

In view of the foregoing, it would be desirable to provide a relatively simple device for selectively adjusting blood flow through a vessel.

It further would be desirable to provide apparatus and methods suited for percutaneous transluminal delivery of a device for selectively adjusting blood flow through a vessel.

It further would be desirable to provide methods that permit adjustment of the device with reduced trauma to the patient and cost relative to previously known methods.

SUMMARY OF THE INVENTION

In view of the foregoing, it is an object of this invention to provide a relatively simple device for selectively adjusting blood flow through a vessel.

It is a further object of the present invention to provide apparatus and methods suited for percutaneous transluminal delivery of a device for selectively adjusting blood flow through a vessel.

It is yet another object of this invention to provide methods that permit adjustment of the device with reduced trauma to the patient and cost relative to previously known methods.

These and other objects of the present invention are accomplished by providing a stent having a deformable constriction, so that after implantation of the stent in, for example, the pulmonary artery, the constriction may be enlarged using a conventional dilatation device.

In a first family of embodiments, the stent comprises a conical or dual-lobed metal or metal alloy mesh that is covered with a biocompatible and elastomeric covering, such as polytetrafluoroethylene (PTFE). The mesh, which may be formed, for example, of stainless steel or a nickel—titanium alloy, includes a constricted region that forms a flow-limiting constriction. Delivery devices are also provided for implanting the stent within a body vessel.

For regulating the flow of blood to the lungs, the stent may be percutaneously and transluminally delivered into the pulmonary artery slightly above the pulmonary valve. After a period of observing the patient, the constricted region of the stent may then be selectively enlarged employing a transluminally delivered dilatation device (e.g., balloon catheter) to adjust the supply of blood to the lungs. If long-term regulation of blood flow is required, the constricted region may be periodically enlarged, as required. During the corrective surgery, the stent may either be retrieved or left in place with the constricted region fully enlarged.

In an alternative embodiment, the stent may again have a conical or dual-lobed shape, and includes a constricted region that forms a flow-limiting constriction. The constricted region is preferably formed of a nickel—titanium alloy having a shape-memory property. In this embodiment, when the constricted region is heated to the austenite phase, for example, by the injection of hot water, the constricted region regains its most constricted form. Whereas in the previous embodiment, the constriction can only be monotonically enlarged, this embodiment of the present invention enables the constricted region to be repeatedly constricted and enlarged, to enable optimization of the size of the constriction.

Methods of implanting the stent of the present invention and for adjusting the degree of constriction are also provided.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

The present invention provides apparatus enabling an interventional approach to regulating the flow of blood through a vessel or organ. While the present invention is described herein in the context of regulating flow through the pulmonary artery to treat congenital heart defects, the stent and deployment apparatus of the present invention may be advantageously used in other applications wherein it is desired to regulate flow through a vessel or organ.

Figure 1A:
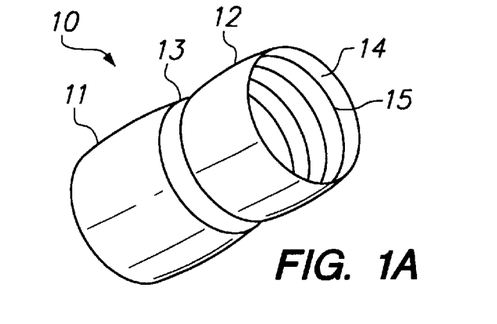
FIGS. 1A and 1B are perspective views from different angles of a first embodiment of a stent constructed in accordance with a first family of embodiments of the present invention.
Figure 1B:
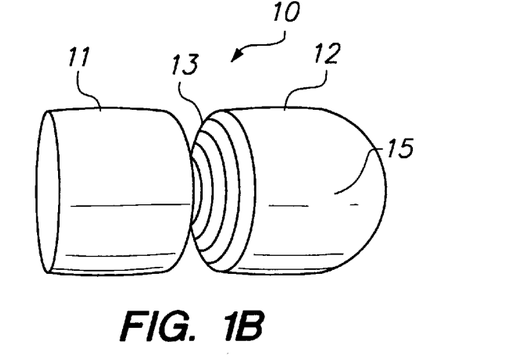

Referring to FIGS. 1A and 1B, illustrative stent 10 constructed in accordance with a first family of embodiments of the present invention is described. Stent 10 comprises an expandable mesh having lobed or conical portions 11 and 12 joined by constricted region 13. At least the interior surface 14 of the stent, and preferably the exterior surface as well, are covered with an elastomeric biocompatible material 15, such as polytetrafluoroethylene (PTFE). Constricted region 13 limits flow through the stent, and therefore may be deployed in a vessel to regulate flow through the vessel. In accordance with the methods of the present invention, the degree of constriction imposed by constricted region 13 on the flow path may be adjusted using previously known dilatation devices to selectively regulate flow through the vessel.

Figure 2A:
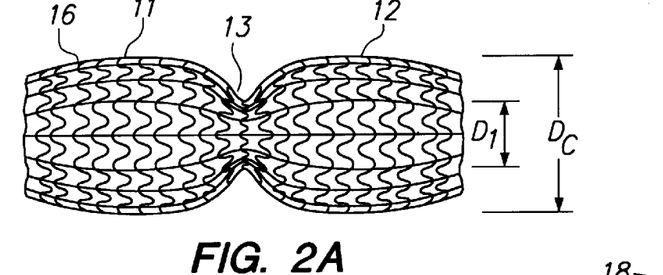
FIGS. 2A and 2B are sectional side views of the stent of FIG. 1 in its contracted and expanded state.

In FIG. 2A, mesh 16 of stent 10 is shown in its contracted delivery configuration (with the cover omitted for clarity), wherein lobes 11 and 12 have contracted diameter $D_C$ and constricted region 13 has reduced diameter $D_1$. Mesh 16 preferably comprises a metal or metal alloy mesh, for example, formed of stainless steel or a nickel—titanium alloy, and may be plastically deformed to deliver the stent as taught in U.S. Pat. No. 4,733,665 to Palmaz, which is incorporated herein by reference.

Figure 2B:
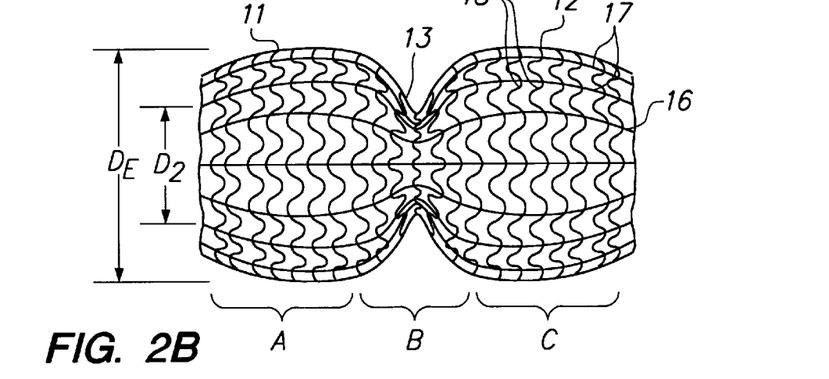

In FIG. 2B, stent 10 is shown in its deployed configuration, wherein lobes 11 and 12 assume deployed diameter $D_E$, while constricted region 13 is expanded to diameter $D_2$. Mesh 16 preferably comprises longitudinal members 17 connected by transverse serpentine connecting members 18, which enable the mesh to be expanded radially outward by dilatation device 20 of FIG. 3. Alternatively, stent 10 may employ any of a number of mesh patterns, such as the slotted configuration shown in the above-incorporated patent, suitable for use in plastically deformable stents.

Stent 10 is manufactured by first forming mesh 16, for example, by weaving or welding together separate longitudinal and transverse elements. Alternatively, the mesh may be formed by chemical etching or laser machining of a thin-walled tube, as described for example, in U.S. Pat. No. 5,421,955 to Lau et al. For example mesh 16 may be formed by chemical etching or laser cutting a tube, after which constricted region 13 is formed by swaging the mid-section of the tube. The transition region, region B in FIG. 2B, from the lobes 11 and 12 to the constricted region 13 should be gradual, so as to avoid the disruption of laminar flow through the stent, and thereby reduce the risk of thrombosis.

Biocompatible material 15 may be disposed on mesh 16, for example, by placing layers of PTFE or other biocompatible polymer material on the interior and exterior surfaces of the mesh, and heating the resulting assembly so that the two layers become sintered together at points of contact through the mesh. Consequently, the mesh becomes embedded between the layers of biocompatible 15.

Figure 3:
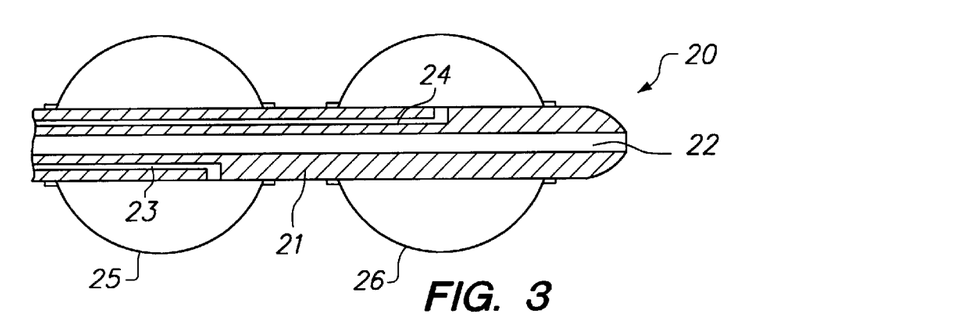
FIG. 3 is a side view of the distal end of an illustrative catheter for use in implanting the stent of FIG. 1.

Referring to FIG. 3, illustrative delivery system 20 for use in deploying stent 10 of the present invention is described. Delivery system 20 includes catheter 21 having guide wire lumen 22, inflation lumens 23 and 24, and balloons 25 and 26. Balloons 25 and 26 are spaced apart longitudinally along the shaft of catheter 21 so that when they are inflated, they cause lobes 11 and 12 of stent 10 to contact the walls of a vessel. Balloons 25 and 26 do not contact the interior surface of constricted region 13 during deployment of stent 10. As will of course be understood, catheter 21 has a length suitable for percutaneous, transluminal deployment of stent 10, and includes a proximal end (not shown) constructed as is well known in the art of catheter design.

Delivery system 20 is preferably formed of materials typically employed in the catheter systems, for example, polyethylene or polyvinyl chloride. Balloons 25 and 26 preferably are either non-compliant or semi-compliant, and may be constructed of polyethylteraphlate (PET), polyurethane or nylon. Balloons 25 and 26 may each have its own inflation lumen 23 and 24, respectively, or may be inflated via a single lumen. Each of balloons 25 and 26 is bonded to the shaft of catheter 20 using techniques which are per se known.

Figure 4A:
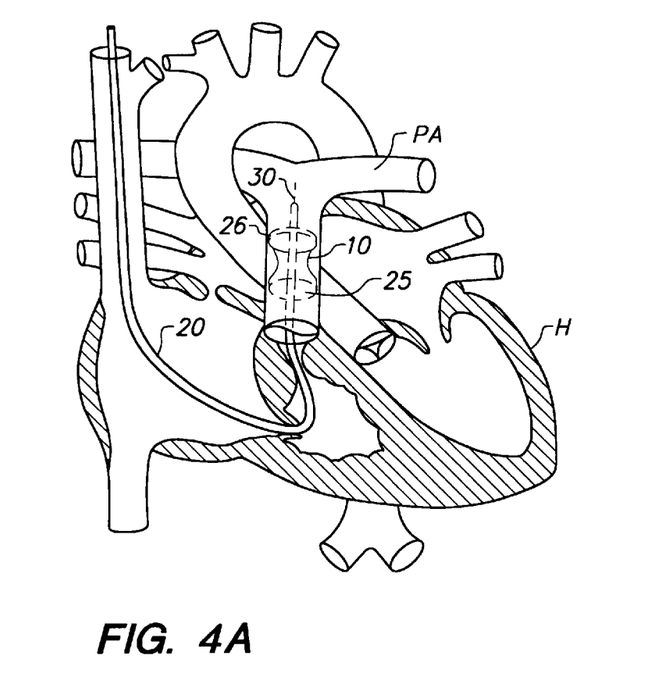
FIGS. 4A to 4C illustrate steps of deploying the stent of FIG. 1 and adjusting the degree of constriction provided by the stent.
Figure 4B:
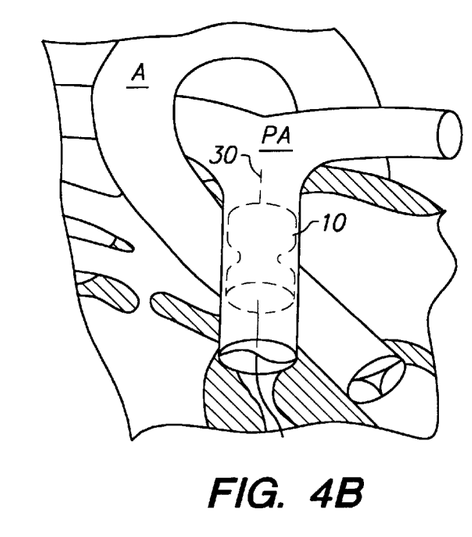
Figure 4C:
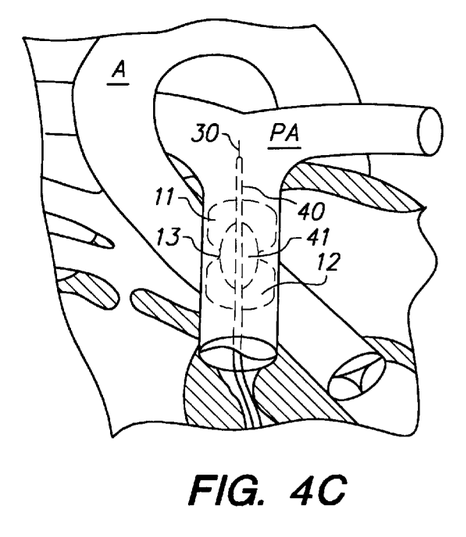

Referring now to FIGS. 4A to 4C, use of stent 10 to regulate blood flow through pulmonary artery PA of heart H having a congenital defect is described. As a first step, stent 10 (in its expanded form) is centered on delivery system 20 so that constricted region 13 is aligned with and spaced between balloons 25 and 26, and the stent is then crimped down onto the balloon to assume its contracted delivery diameter. The delivery system is percutaneously and transluminally inserted into pulmonary artery PA via, for example, the jugular vein, superior vena cava and right atrium along pre-placed guide wire 30. Once the stent is disposed in the pulmonary artery, for example, as determined by conventional fluoroscopic techniques, balloons 25 and 26 are inflated to radially expand lobes 11 and 12 of the stent into intimate contact with the wall of the pulmonary artery, as shown in FIG. 4A.

With respect to FIG. 4B, once stent 10 has been deployed in the pulmonary artery, balloons 25 and 26 are deflated, and delivery system 20 is withdrawn. Guide wire 30 is left in place. The patient is then monitored for a period of time (i.e., sufficient for the flow to become stabilized) to assess whether the blood supply to the lungs is adequate with constricted region 13 at its maximum degree of flow constriction. For example, the blood oxygen saturation level may be monitored to assess adequate flow to the lungs while the heart rhythm may be monitored to ensure that the heart is not being overworked.

If it is determined that the constricted region creates too large a flow impedance, a previously known balloon dilatation catheter 40 may be inserted along guide wire 30. Balloon 41 of dilatation catheter 40 preferably is non-compliant, so that complete expansion of the balloon will result in an predetermined increment in the diameter of the constricted region 13 of stent 10. As shown in FIG. 4C, balloon 41 may then be dilated to expand constricted region 13 by the predetermined amount. Balloon 41 is then deflated and dilatation catheter 40 is removed. The patient's vital signs may then be monitored for another period of time.

If, at the end of this period, the blood oxygen saturation and heart signals appear acceptable, guide wire 30 may be removed, completing the procedure. If, on the other hand, further reduction in the degree of flow impedance created by the constriction is required, a dilatation catheter having a slighter larger balloon may be employed to further enlarge the diameter of the constricted region. The step of incrementally increasing the diameter $D_2$ of the constricted region preferably is repeated as many times as necessary to achieve a desired degree of flow regulation.

Figures 5A, 5B, 5C:
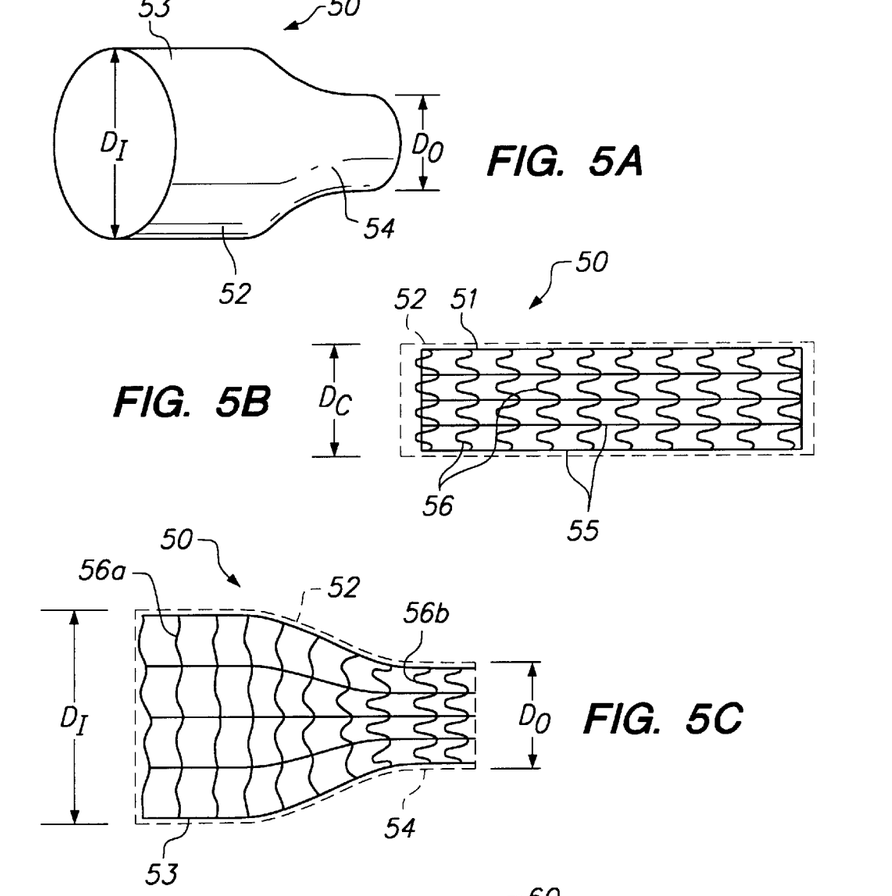
FIGS. 5A through 5C are, respectively, a perspective view of a second embodiment of a stent constructed in accordance with the first family of embodiments of the present invention, and sectional side views of the stent in its contracted and expanded state.

Referring now to FIGS. 5A to 5C, stent 50, which is an alternative member of the first family of embodiments is described. As in the embodiment of FIG. 1, stent 50 comprises mesh 51 (detail omitted for clarity in FIG. 5A) covered with an elastomeric, biocompatible covering 52, such as PTFE. Stent 50, when deployed, includes conical portion 53 having inlet diameter $D_I$ and constricted region 54 having outlet diameter $D_O$. Constricted region 54 limits flow through the stent, and therefore may be deployed in a vessel to regulate flow through the vessel. In accordance with the methods of the present invention, the degree of constriction imposed by constricted region 54 on the flow path may be adjusted using previously known dilatation devices to selectively regulate flow through the vessel.

In FIG. 5B, stent 50 is shown in its contracted delivery configuration (with covering 52 shown in dotted line for clarity), wherein the stent has a contracted diameter $D_C$. Mesh 51 preferably comprises a metal or metal alloy mesh, for example, formed of stainless steel or a nickel—titanium alloy, and may be plastically deformed to deliver the stent as taught in U.S. Pat. No. 4,733,665 to Palmaz and U.S. Pat. No. 5,421,955 to Lau et al. Elastomeric and biocompatible covering 52 may be affixed to the mesh as described hereinabove.

Figure 6:
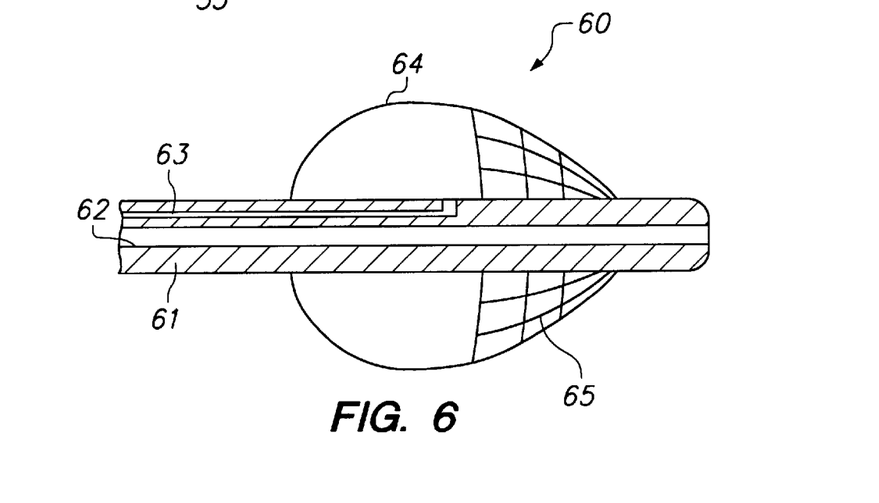
FIG. 6 is a side view of the distal end of an illustrative catheter for use in implanting the stent of FIG. 5.

Mesh 51 preferably comprises longitudinal members 55 connected by transverse serpentine connecting members 56, which enable the mesh to be expanded radially outward by conical balloon 64 of delivery device 60 (see FIG. 6). Alternatively, stent 50 may employ any of a number of mesh patterns, and may be formed by weaving or welding together separate longitudinal and transverse elements, or chemical etching or laser machining a thin walled tube, such as described in the above-incorporated Palmaz and Lau et al. patents.

In FIG. 5C, stent 50 is shown in its deployed configuration, wherein conical region 53 assumes deployed diameter $D_I$, while constricted region 54 has diameter $D_O$. When expanded to its deployed configuration, transverse serpentine connecting members 56 in conical portion 53 are deformed to form approximately straight circumferential segments 56a, while the transverse serpentine members in constricted region 54, such as members 56b, retain much of the original serpentine pattern. Accordingly, members 56b may be expanded radially outward as needed to reduce the degree of constriction imposed by constricted region 54.

Referring to FIG. 6, illustrative delivery system 60 for use in deploying stent 50 of FIG. 5 is described. Delivery system 60 includes catheter 61 having guide wire lumen 62, inflation lumen 63 and conical balloon 64. Balloon 64 preferably has net 65 embedded within its thickness that provides the balloon with a conical shape when deployed. Balloon 64 is sized to fit within and radially expand conical region 53 of stent 50, but does not expand constricted region 54 during deployment of the stent. As will of course be understood, catheter 61 has a length suitable for percutaneous, transluminal deployment of stent 50, and includes a proximal end (not shown) constructed as is well known in the art of catheter design.

Delivery system 60 is preferably formed of materials typically employed in the catheter systems, for example, polyethylene or polyvinyl chloride. Balloon 64 preferably is either non-compliant or semi-compliant, and may be constructed of polyethylteraphlate (PET), polyurethane or nylon. Net 65 may comprise wire formed from stainless steel or a high strength polymer (e.g., monofilament polyesther), and may either be embedded in the wall thickness of balloon 64 or affixed to its outer surface. Balloon 64 is inflated via inflation lumen 63 and is bonded to the shaft of catheter 60 using techniques which are per se known.

Figure 7A:
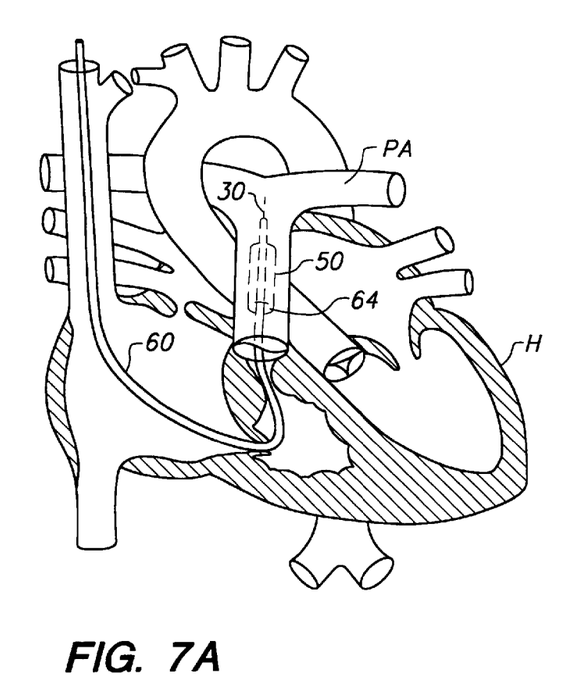
FIGS. 7A to 7C illustrate steps of deploying the stent of FIG. 5 and adjusting the degree of constriction provided by the stent.
Figure 7B:
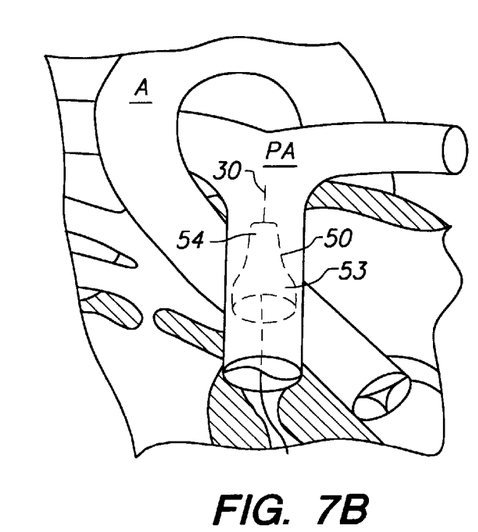
Figure 7C:
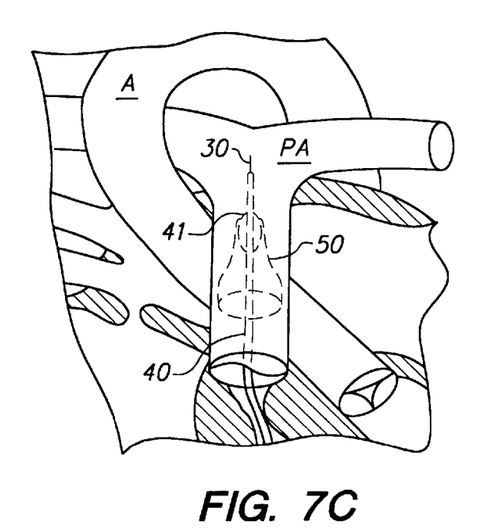

Referring now to FIGS. 7A to 7C, use of stent 50 to regulate blood flow through pulmonary artery PA of heart H having a congenital defect is described. As a first step, stent 50 is crimped onto delivery system 60 so that conical region 53 is aligned with balloon 64. The delivery system is percutaneously and transluminally inserted into pulmonary artery PA along pre-placed guide wire 30. Once the stent is disposed in the pulmonary artery, for example, as determined by conventional fluoroscopic techniques, balloon 64 is inflated to radially expand conical portion 53 of the stent into intimate contact with the wall of the pulmonary artery, as shown in FIG. 7B.

With respect to FIG. 7B, once stent 50 has been deployed in the pulmonary artery, balloon 64 is deflated, and delivery system 60 is withdrawn. Guide wire 30 is left in place. As in the method described hereinabove with respect to stent 10, the patient is then monitored for a period of time to assess whether the blood supply to the lungs is adequate with constricted region 54 at its maximum degree of flow constriction.

If it is determined that the constricted region creates too large a flow impedance, a previously known balloon dilatation catheter 40 may be inserted along guide wire 30. Balloon 41 of dilatation catheter 40 preferably is non-compliant, so that complete expansion of the balloon will result in an predetermined increment in outlet diameter $D_O$ of the constricted region 54. As shown in FIG. 7C, balloon 41 may then be dilated to expand constricted region 54 by the predetermined amount. Balloon 41 is then deflated and dilatation catheter 40 is removed. The patient's vital signs may then be monitored for another period of time, and constricted region 54 may be further expanded to achieve a desired degree of flow regulation. Upon completion of the procedure, guide wire 30 is removed.

Referring again to FIG. 2B, a stent constructed in accordance with an alternative family of embodiments of the present invention is described. This embodiment, which is visually identical to stent 10 of FIGS. 1A to 2B, differs in that regions A and C (i.e., conical portions or lobes 11 and 12) are formed of a plastically deformable material, e.g., stainless steel, while region B comprises a material exhibiting a shape-memory property. For example, region C may comprise a nickel—titanium alloy having an austenite transition temperature slightly higher than body temperature (e.g. 40° C.). Region C therefore assumes its minimum expanded diameter $D_2$ when exposed to a high temperature fluid. Accordingly, when the implanted stent is exposed to, for example, heated saline, the constricted region recovers its maximum degree of flow impedance.

In this alternative embodiment, the constricted region is capable of being deformably expanded by a dilatation device, but recovers its original shape when briefly raised above the austenite transition temperature. Constricted region C therefore functions in a fashion similar to the heat-recoverable stent described in U.S. Pat. No. 5,197,978 to Hess, incorporated herein by reference, while the lobes in regions A and C retain the stent firmly implanted in the vessel.

As will be readily understood, a stent constructed in accordance with this family of embodiments of the present invention enables the clinician to optimize the degree of flow regulation provided by the stent. In particular, if the degree of flow impedance is reduced too much by overenlarging the diameter of the constricted region, the stent may be flushed with heated saline so that the constricted region recovers its maximum degree of impedance. The constricted region may then be re-enlarged to a diameter slightly less than that determined to be too large in the previous iteration.

Figure 8A:
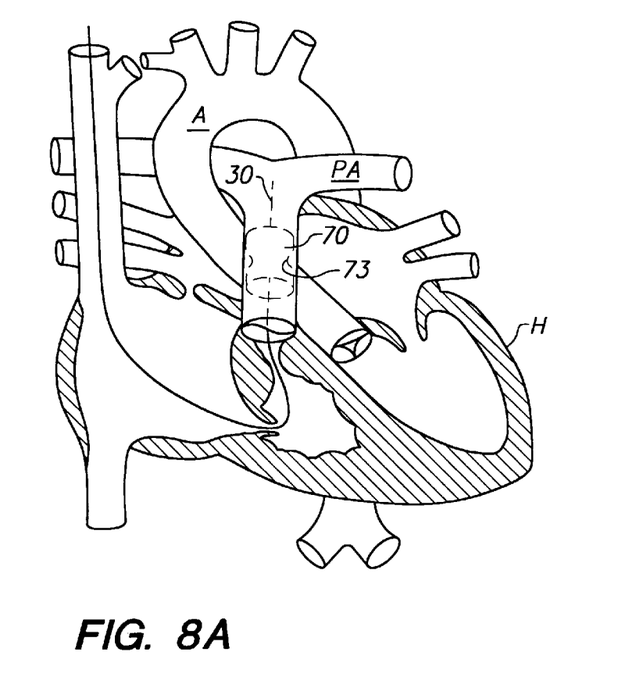
FIGS. 8A to 8C illustrate steps of employing an illustrative embodiment of a stent constructed in accordance with a second family of embodiments of the present invention.
Figure 8B:
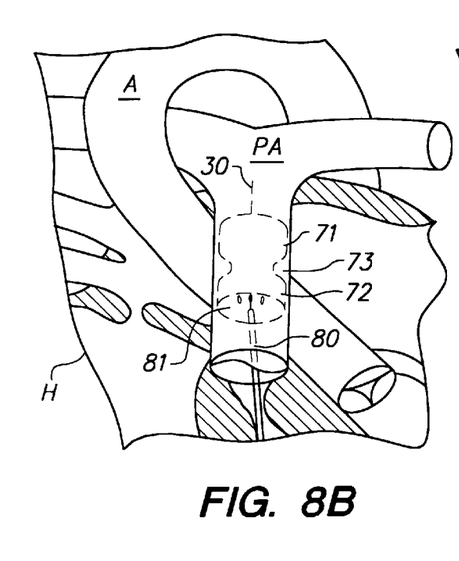
Figure 8C:
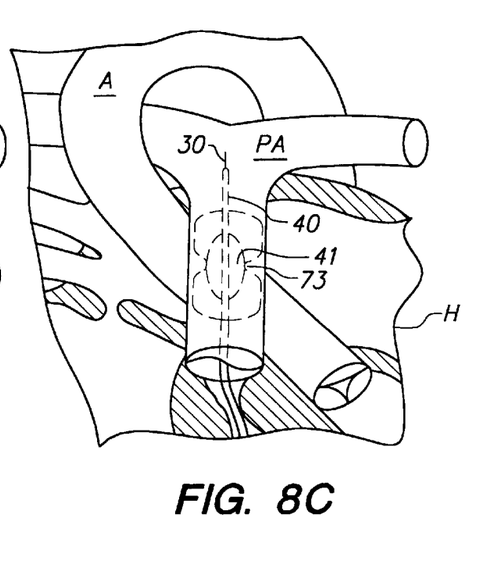

Referring now to FIGS. 8A to 8C, methods of using stent 70 constructed in accordance with the second family of embodiments of the present invention is described. In FIG. 8A, stent 70 is shown deployed in pulmonary artery PA of heart H having a congenital defect, in accordance with the methods described hereinabove with respect to FIGS. 4A to 4C. In accordance with those methods, the clinician iterates the steps of enlarging the diameter of the constricted region, and monitoring the patient's vital signs. Let it be assumed however, that after a step of enlarging the diameter of constricted region 73, it is determined by conventional techniques that the heart is being overworked because the diameter of the constricted region has been overenlarged.

In accordance with this aspect of the present invention, catheter 80 is positioned adjacent to stent 70 and injects a stream of heated fluid 81, e.g., saline, into the stent for a period of time sufficient to raise the temperature of constricted region 73 into the austenite phase, as illustrated in FIG. 8B. Upon transitioning to the austenite phase, constricted region 73 contracts to its minimum expanded diameter $D_2$, while plastically deformed lobes 71 and 72 hold stent 70 securely in position in the vessel.

In FIG. 8C, previously known balloon dilatation catheter 40 having a desired expanded diameter (determined from the previous steps of iteratively enlarging the diameter of the constricted region and monitoring the patient's response) may then be inserted along guide wire 30. Once positioned within constricted region 73 of stent 70, balloon 41 is dilated to expand constricted region 73 to the diameter judged by the clinician to provide the optimum degree of flow regulation.

The foregoing description provides an illustrative use of the stents and methods of the present invention for regulating the flow of blood in the pulmonary artery. Other applications for the present invention will be apparent to those of skill in interventional therapy. For example, a stent may be configured so that the expanded diameter $D_2$ (or outlet diameter $D_O$) of the constricted region has a relatively small diameter, thus permitting use of the stent as an occlusive device. Alternatively, for the stent of FIGS. 1 and 2, the expanded diameters of the first and second lobes may be different. In addition, for the embodiment including a heat recoverable constricted region, other means may be employed to heat the stent, from radiative heating techniques to resistive techniques, as described in the above-incorporated U.S. Pat. No. 5,197,978.

While preferred illustrative embodiments of the invention are described above, it will be apparent to one skilled in the art that various changes and modifications may be made therein without departing from the invention, and the appended claims are intended to cover all such changes and modifications that fall within the true spirit and scope of the invention.

What is claimed is:

1. Apparatus for regulating flow through a vessel or organ, the apparatus comprising a tubular member having first and second ends, an interior surface forming a lumen extending between the first and second ends, and a constricted region disposed between the first and second ends, a portion of the tubular member adjacent the first end having a substantially uniform first diameter along a first length and the constricted region having a second diameter smaller than the first diameter, the constricted region formed by a radial inward extension of the interior surface, the tubular member having a contracted configuration suitable for transluminal delivery, and a deployed configuration wherein the portion of the tubular member adjacent to the first end engages a wall of the vessel or organ along the first length and the constricted region limits flow through the lumen, wherein the constricted region comprises a plastically deformable material and has a continuous curved profile that gradually transitions between the first diameter and the second diameter to reduce thrombus formation, and wherein the second diameter, in the deployed configuration, is adapted to be selectively enlarged by application of a radially outwardly directed force on the interior surface of the constricted region to obtain an adjustable degree of constriction, and is restored to a minimum diameter by application of heat to the constricted region.

2. The apparatus as defined in claim 1 wherein the tubular member further comprises a portion of the tubular member adjacent the second end having a diameter greater than the second diameter, the portion of the tubular member adjacent to the second end engaging the wall of the vessel or organ in the deployed configuration.

3. The apparatus as defined in claim 1 wherein the tubular member comprises a mesh covered with a biocompatible material.

4. The apparatus as defined in claim 3 wherein the biocompatible material is elastomeric.

5. The apparatus as defined in claim 3 wherein the mesh comprises a deformable metal or metal alloy.

6. The apparatus as defined in claim 3 wherein the mesh comprises a plurality of longitudinal members interconnected by serpentine transverse members.

7. The apparatus as defined in claim 3 wherein the constricted region of the mesh comprises a shape-memory material.

8. The apparatus as defined in claim 1 wherein the tubular member has a contracted configuration for transluminal delivery and a deployed configuration wherein a portion of the tubular member adjacent the first end engages the wall of the vessel or organ, the tubular member expanding from the contracted configuration to the deployed configuration by application of a radially outwardly directed force on the interior surface.

9. The apparatus as defined in claim 1 wherein the radial inward extension of the interior surface of the tubular member in the constricted region constitutes a gradual transition from the first diameter.

10. Apparatus for regulating flow through a vessel or organ, the apparatus comprising:

a tubular member having first and second ends and an interior surface forming a lumen extending through the tubular member, the tubular member having a contracted configuration configured for percutaneous delivery and a deployed configuration, wherein a first portion of the tubular member is adapted to expand to a substantially uniform first diameter along a first length to engage a wall of the vessel or organ along the first length and a second portion of the tubular member includes a radial inward extension of the interior surface forming a constricted region having a second diameter smaller than the first diameter, the constricted region limiting flow through the lumen; and an elastomeric and biocompatible cover disposed on a surface of the tubular member, wherein the constricted region is plastically deformable and has a continuous curved profile that gradually transitions between the first diameter and the second diameter to reduce thrombus formation, wherein the second diameter is adapted to be selectively enlarged by application of a radially outwardly directed force on the interior surface of the constricted region to obtain an adjustable degree of constriction, and wherein the second diameter is restored to a minimum diameter, in the deployed configuration, by application of heat to the constricted region.

11. The apparatus as defined in claim 10 wherein the tubular member further comprises a third portion having the first diameter, the third portion adapted to engage the wall of the vessel or organ in the deployed configuration.

12. The apparatus as defined in claim 10 wherein the tubular member is adapted to expand from the contracted configuration to the deployed configuration by application of a radially outwardly directed force on the interior surface.

* * * * *